US009152762B2

(12) United States Patent
Boyer et al.

(10) Patent No.: US 9,152,762 B2
(45) Date of Patent: Oct. 6, 2015

(54) SYSTEM, METHOD, AND SOFTWARE FOR POSITIVE PATIENT IDENTIFICATION

(71) Applicant: Covidien LP, Mansfield, MA (US)

(72) Inventors: Robert T Boyer, Longmont, CO (US); Richard M. Batch, Longmont, CO (US)

(73) Assignee: Covidien LP, Mansfield, MA (US)

( * ) Notice: Subject to any disclaimer, the term of this patent is extended or adjusted under 35 U.S.C. 154(b) by 114 days.

(21) Appl. No.: 13/768,268

(22) Filed: Feb. 15, 2013

(65) Prior Publication Data

US 2014/0236922 A1   Aug. 21, 2014

(51) Int. Cl.
*G06F 17/30* (2006.01)
*G06F 19/00* (2011.01)

(52) U.S. Cl.
CPC ............ *G06F 19/322* (2013.01); *G06F 19/323* (2013.01)

(58) Field of Classification Search
USPC ............... 707/722; 382/128; 705/3; 383/128; 378/98.5
See application file for complete search history.

(56) References Cited

U.S. PATENT DOCUMENTS

| | | | |
|---|---|---|---|
| 4,857,716 A | 8/1989 | Gombrich et al. | |
| 5,071,168 A | 12/1991 | Shamos | |
| 5,381,487 A | 1/1995 | Shamos | |
| 6,922,148 B2 | 7/2005 | Despotis | |
| 7,436,986 B2 | 10/2008 | Caldwell | |
| 7,683,759 B2 | 3/2010 | Martis et al. | |
| 8,284,024 B2 | 10/2012 | Toleti et al. | |
| 8,308,640 B2 | 11/2012 | Baldus et al. | |
| 8,339,262 B2 | 12/2012 | Pless | |
| 2002/0101619 A1* | 8/2002 | Tsubaki et al. | 358/302 |
| 2006/0159325 A1* | 7/2006 | Zeineh et al. | 382/128 |
| 2009/0048871 A1* | 2/2009 | Skomra | 705/3 |
| 2009/0184842 A1 | 7/2009 | Baldus et al. | |
| 2010/0277274 A1 | 11/2010 | Toleti et al. | |
| 2012/0051521 A1* | 3/2012 | Nishino | 378/98.5 |
| 2012/0191476 A1* | 7/2012 | Reid et al. | 705/3 |
| 2013/0197941 A1* | 8/2013 | Cochran | 705/3 |
| 2014/0006943 A1* | 1/2014 | Robbins et al. | 715/273 |

* cited by examiner

*Primary Examiner* — Jeffrey A Burke
*Assistant Examiner* — Thong Vu
(74) *Attorney, Agent, or Firm* — Carter, DeLuca, Farrell & Schmidt, LLP (57) ABSTRACT

A system including a database storing a plurality of patient data corresponding to a plurality of patients, where the patient data corresponds to a particular patient and includes at least one image of the particular patient; and a component configured to receive patient identification information previously assigned to one of the particular patients, extract the patient data corresponding to the particular patient identification information received, and display the patient data on a display including at least one image of the particular patient.

20 Claims, 8 Drawing Sheets

SYSTEM, METHOD, AND SOFTWARE FOR POSITIVE PATIENT IDENTIFICATION

TECHNICAL FIELD

The present disclosure relates generally to positive patient identification, and more particularly to a system, method, and software for positive patient identification.

BACKGROUND

When monitoring a patient, a medical device may collect and display information about that patient. The medical devices may collect information through one or more of a variety of ways, such as a patient interface that measures a physiological condition, or a user interface that collects information input by a user. The collected information may then be received by a data collection server for processing and subsequent use by clinicians.

SUMMARY

Aspects of the present disclosure are directed to a system, method, and computer readable recording medium capable of receiving patient identification information, searching a database for the corresponding patient data associated with the patient identification information, and displaying the patient data with an image of the patient.

By displaying patient data including an image of the patient clinicians may confirm, or otherwise verify, the identity of the patient. In some cases, medical devices may be monitoring the patient and transmitting the patient parameters to a data collection server for processing and storage in association with the patient. With the image of the patient displayed, the clinician may verify that the patient parameters being transmitted are properly associated with the particular patient in which they are monitoring.

Certain embodiments of the present disclosure may include some, all, or none of the above advantages. One or more other technical advantages may be readily apparent to those skilled in the art from the figures, descriptions, and claims included herein. Moreover, while specific advantages have been enumerated above, various embodiments may include all, some, or none of the enumerated advantages.

BRIEF DESCRIPTION OF THE DRAWINGS

For a more complete understanding of the present disclosure and its features and advantages, reference is now made to the following description, taken in conjunction with the accompanying drawings, in which.

DETAILED DESCRIPTION

The present disclosure incorporates the use of patient images to verify and/or match patients with their corresponding patient identification information by transmitting an image of the patient to a remote device for clinician confirmation. By verifying and matching the patient identification information, the patient parameters, which are transmitted via medical devices that are monitoring the patient, may be processed and stored with a greater degree of certainty that the patient parameters are the patient parameters of the patient associated with the particular patient identification information entered and not that of another patient. After associating the medical devices with the particular patients, the patient parameters captured by the medical devices may be processed, stored, and reviewed by clinicians for diagnoses and patient monitoring. It is desirable to associate the correct patient parameters with the proper patients so that the patient parameters processed, stored, or otherwise reviewed by the clinician are correct for a particular patient.

Figure 1:
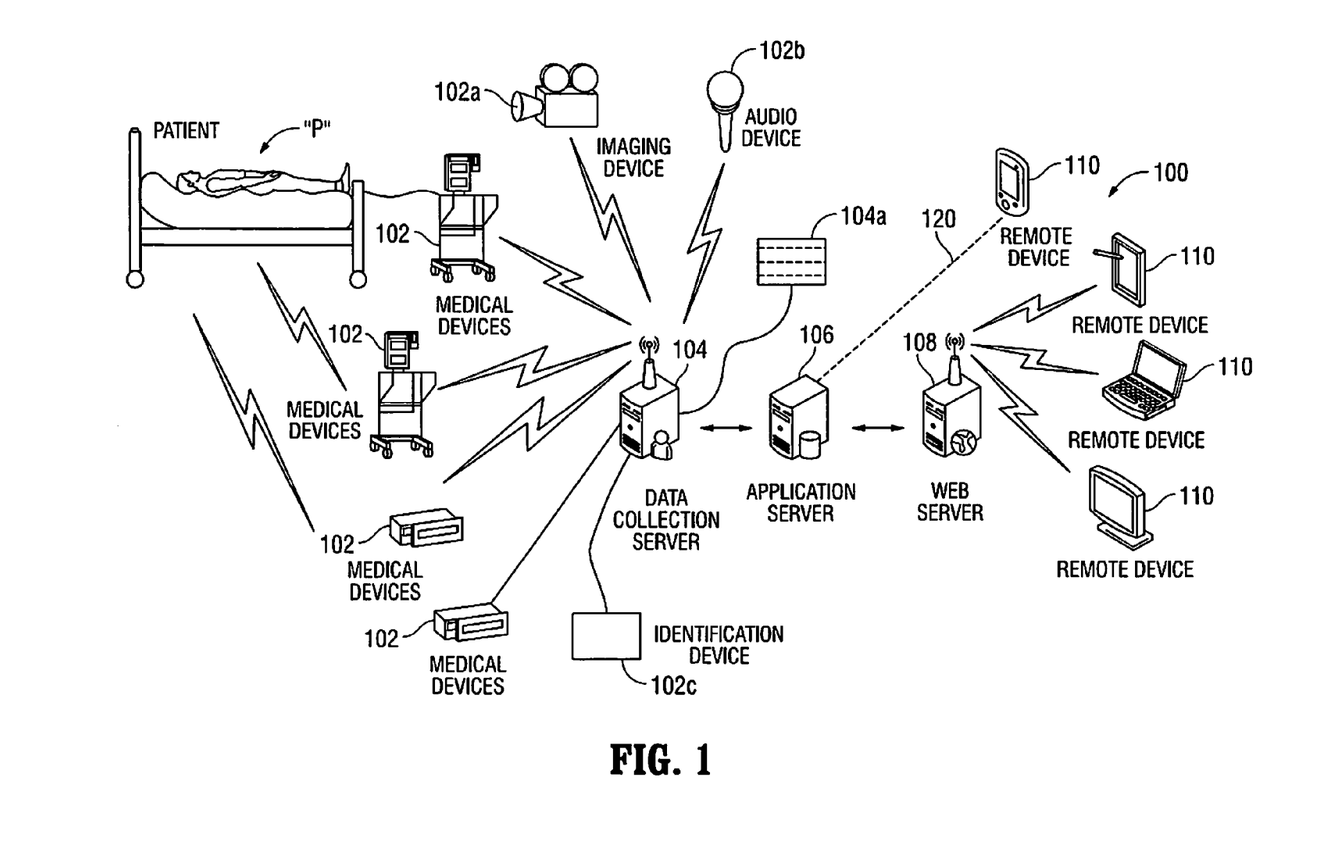
FIG. 1 illustrates an example system for positive patient identification, according to certain embodiments of the present disclosure.

FIG. 1 illustrates an example system 100 for positive patient identification, according to certain embodiments of the present disclosure. System 100 includes one or more medical devices 102, an imaging device 103, a data collection server 104, an application server 106, a web server 108, and one or more remote devices 110. System 100 may further include an audio device 109 and an identification device 111.

Although this particular implementation of system 100 is illustrated and primarily described, the present disclosure contemplates any suitable medical network implementation of system 100 according to particular needs of the institution or facility. In particular, it is envisioned that system 100 may include some or all of the components described herein. Moreover, although each of the components of system 100 are illustrated and described as separate units, it is understood that any of the components of system 100 may be combined with another component as a single component. For example, although imaging device 103 is shown and described as a separate component from mobile device 110, in a particular embodiment mobile device 110 includes an imaging device similar to imaging device 103.

Each patient "P" is associated with, or assigned, patient identification information. Typically, a patient is assigned patient identification upon being admitted to a medical facility. The patient identification information includes any type of information or data suitable for identifying the patient or differentiating one patient from another, and/or any other means which may be used for looking up the patient data associated with a particular patient. In some embodiments, patient identification information includes the patient's name, a number, a barcode, or data embedded in a radio frequency identification chip. Typically, the patient identification information is physically displayed on, or otherwise secured to, the patient. In certain embodiments, as will be described in further detail below with reference to FIG. 3, the patient identification information is displayed via a wristband attached to the patient's wrist.

Medical devices 102, imaging device 103, and/or audio device 109 generate patient data, such as and without limitation, patient parameters, data relating to the identity of the patient "P," physiological parameters of the patient, and image or audio data of the patient. System 100 collects the data and stores it, for example on data collection server 104. The system 100 uses one or more of servers 104, 106, and 108 to process the data and using various protocols and software transforms the data such that it can be readily accessed and analyzed via one or more graphic user interfaces (GUI), including some that might be viewed on remote devices 110. System 100 may be configured to store the patient data in a database 104a and associate the patient data with a particular patient.

Continuing with reference to FIG. 1, each medical device 102 is communicatively coupled to data collection server 104, which stores the patient data in a database 104a and associates the patient data with the particular patient being monitored. Application server 106 retrieves the patient data from the database 104a and process the patient data. Additionally, Application server 106 receives patient identification information, and in response to receiving the patient identification information, transmits patient image data in the form of an image of the patient to mobile device 110. A web server 108 may be employed to publish the patient data processed by the application server 106, such that it may be viewed on a GUI on a remote device 110, thereby enabling clinicians using the remote device 110 to view and analyze the patient data from remote locations. In this context, remote can mean any location not immediately adjacent, or immediately adjacent, to the patient and may include a hospital floor nurse's station, a central alarm monitoring station for a hospital, and smartphones or tablets operated by a clinician, e.g., an on-call physician far removed from the patient.

As noted above, system 100 includes one or more medical devices 102. In certain embodiments, the medical devices 102 generate and store patient data, such as patient parameters, whether generated by monitoring of the patient or input into the medical device 102 by a clinician. As described above, patient data may include any patient identifiers, patient parameters, medical history, clinician notes, alarm thresholds, alarm events, device settings, measurements of values indicating physiological conditions such as oxygen saturation levels, pulse rates, heart rates, other vital signs, and any other data input to or output from medical devices 102. Medical devices 102 may be any devices that are used for monitoring, tracking or treating patients. For example, medical devices 102 may include a ventilator connected to a patient to deliver respiration therapy, a pulse oximeter that monitors the oxygen saturation of a patient's blood, a device for tracking a patient within a hospital with or without monitoring a physiological condition, as well as other medical devices known to those of skill in the art.

Medical devices 102 include a component for identifying the particular medical device 102, including, but not limited to, radio frequency identification chips and unique bar codes. Additionally, medical devices 102 are capable of transmitting the patient data to the data collection server 104 directly, which may include identification data of the medical device and patient data, such as patient parameters.

As noted above, system 100 includes one or more imaging devices 103, which generate images that are to be associated with patient data. In particular, imaging device 103 generates patient image data in the form of an image of the patient. In an embodiment, imaging device 103 is a component of mobile device 110. Patient image data generated by imaging device 103 may include a single image, multiple images, and/or video of a patient for storage in the database 104a in association with the particular patient identification information. Imaging device 103 is configured to capture an image of the patient and send that captured image as patient image data to the data collection server 104 for association with a particular patient, via the patient identification information, and storage in the database 104a.

Imaging device 103 may include, without limitation, one or more digital charge-coupled devices (CCD), complementary metal-oxide-semiconductor (CMOS) active pixel sensor, or combinations/hybrids of the two, whether for capturing visible or infrared spectrum light, as well as other image sensors known to those of skill in the art.

As noted above, in addition to performing a medical function, medical devices 102, imaging device 103, and/or audio device 109 may generate patient data. For example, the ventilator may generate data indicating the average volume of air expelled in each breath, or the respiratory rate of a patient. This patient data may be stored locally on the medical device 102 or output to a data collection server 104, or both. The ventilator may also store or output to the data collection server 104 data identifying the settings of the ventilator and whether any alarms have been triggered. The patient data from the medical device 102, imaging device 103, and/or audio device 109 may be constantly streamed, periodically posted to the data collection server 104, or the data collection server 104 may periodically poll the medical device 102. Further, other protocols may be employed based on alarming conditions, such that the data collection server 104 receives important data in a timely manner, regardless of any set period for collection of the patient data.

Medical devices 102, imaging device 103, and/or audio device 109 are communicatively coupled to data collection server 104 via a network such as a LAN, WAN, or WiLAN employing one or more of well known network communication protocols. In certain embodiments, medical devices 102, imaging device 103, and/or audio device 109 are also communicatively coupled to the application server 106, web server 108, and remote devices 110.

Data collection server 104 includes one or more electronic computing devices operable to receive, transmit, process, and store data associated with system 100. In addition, data collection server 104 may use any suitable operating system, as would be understood by those of skill in the art. Although a single data collection server 104 is illustrated, the present disclosure contemplates system 100 including any suitable number of data collection servers 104. Moreover, although referred to as a data collection server, the present disclosure contemplates data collection server 104 comprising any suitable type of processing device or devices.

Data collection server 104 may map received patient data, images, and medical devices 102 to match internal fields in a storage unit 104a, also referred to herein as a database 104a, according to certain embodiments. Database 104a includes stored images of a plurality of different patients as patient image data, and the stored images are identifiable via the patient identification information. Data collection server 104 is configured to receive patient identification information, for example from a remote device 100, search the database 104a for the corresponding patient data associated with the patient identification information, and deliver the patient image data, i.e. an image of the patient, associated with the patient identification information to the remote device 110. In addition, data collection server 104 is configured to receive a confirmation from a remote device 110 that the image of the patient is the correct image associated with the patient identification information. In addition, the data collection server 104 is configured to send the patient parameters to the remote device 110 once a confirmation is received.

The stored patient data in the database 104a, or otherwise on the data collection server 104, may be accessed by application server 106. Application server 106 includes one or more electronic computing devices operable to receive, transmit, process, and store data associated with system 100. In addition, application server 106 uses any suitable operating system. Although a single application server 106 is illustrated, the present disclosure contemplates system 100 including any suitable number of application servers 106. Moreover, although referred to as an application server, the present disclosure contemplates application server 106 comprising any suitable type of processing device or devices.

According to one embodiment, application server 106 runs one or more applications through which the data collected by the data collection server 104 can be processed and made presentable to a user. In one example, the application server 106 includes a data service that runs on a conventional web service platform for transmitting data to web server 108. Application server 106 may include a database server in certain embodiments. According to one embodiment, application server 106 includes a logical system that executes an algorithm, such as a clinical application using patient data. For example, application server 106 may process the patient data, and the processed data may then be transmitted to web server 108.

Continuing with reference to FIG. 1, system 100 includes one or more web servers 108. Web server 108 includes one or more electronic computing devices operable to receive, transmit, process, and store data associated with system 100, and uses any suitable operating system. Moreover, although referred to as a web server, the present disclosure contemplates web server 108 comprising any suitable type of processing device or devices.

According to one embodiment, web server 108 creates a data service that publishes a conventional web services platform, which receives data from application server 106, transmits data to remote devices 110, and receives data from remote devices 110 for distribution back to the application server 106 and the data storage server 104. For example, web server 108 may receive data from application server 106 and transmit data, upon request to remote devices 110.

Although FIG. 1 depicts separate devices for data collection server 104, application server 106, and web server 108, it will be readily apparent that the functions of these devices may be combined into just two servers or even a single device that receives patient data from medical devices 102, imaging device 103, and/or audio device 109, and processes the patient data such that it can be displayed on one or more remote devices 110. It will also be understood that the functions may be allocated differently than shown, with application server 106 additionally performing the functions of web server 108 or the functions of data collection server 104.

Figure 2:
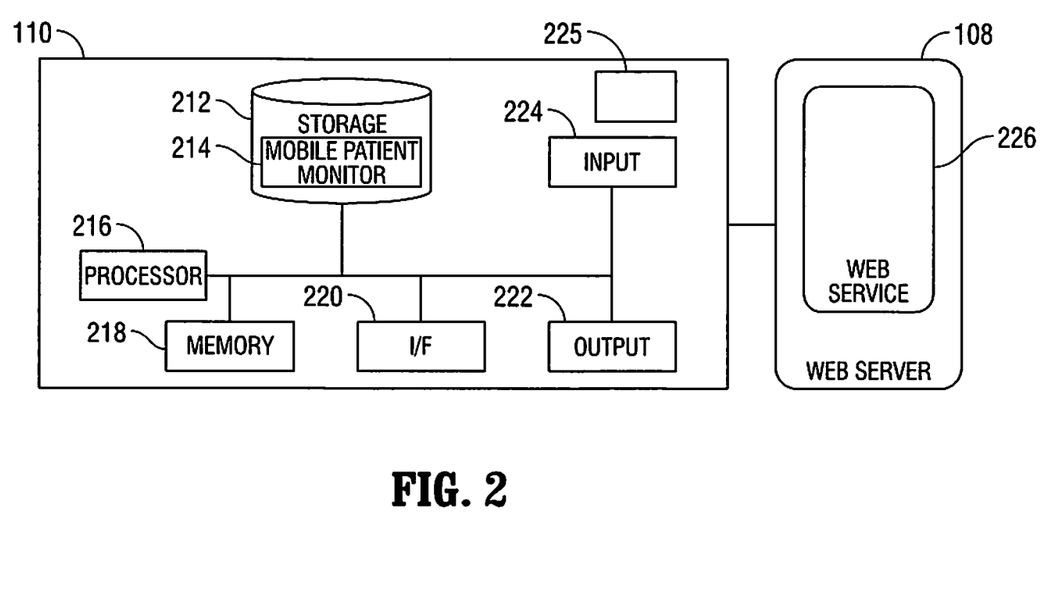
FIG. 2 is a schematic illustration of an example remote device of the system for positive patient identification in FIG. 1, according to certain embodiments of the present disclosure.

FIG. 2 illustrates an example remote device 110 of system 100, according to certain embodiments of the present disclosure. Remote devices 110 may be any device that provides output to, and can receive input from, a user, such as a clinician. Each remote device 110 includes one or more computer systems at one or more locations. In certain embodiments, output at remote devices 110 includes vibrations, display views including pop-up messages, sound, or any combination desired. In some embodiments, remote devices 110 connect directly to application server 106 through a direct socket connection, as indicated by reference number 120 in FIG. 1. In such instances, the remote device 110 is able to connect directly to the applications running on the application server 106, and does not require the use of the web server 108. Such a configuration may be useful for accessing the patient data at locations within a hospital or medical facility such as at a nurse's monitoring station or a general hospital patient monitoring station. Direct connection to the application server 106 may, in some instances, provide greater access to the patient data as well as greater options for refinement or distillation of the data, as would be understood by those of skill in the art, when compared to the data made available via the web server 108 for review by remote devices.

Each remote device 110 includes input components (such as a keypad, touch screen, mouse, or other device that can accept input), output devices, mass storage media, or other suitable components for receiving, processing, storing, and communicating data.

According to one embodiment, remote devices 110 display one or more web pages hosted by application server 106 and/or web server 108 and display data relating to a patient and the medical devices 102 to which the patient is connected. The remote device 110 also receive data from any of the components of system 100, and transmit data to any of the components of system 100. For example, a clinician may activate a browser on remote device 110 and navigate to a web page hosted by web server 108. The browser renders the web page, which includes data processed by application server 106 and/or data collection server 104. The web page provides a summary of all medical devices 102, imaging device 103, and/or audio device 109 under a clinician's responsibility. In addition, the web page may enable a detailed view that displays specific device data, therapy parameter data, and alarm status data.

Remote device 110 is communicatively coupled with a web server 108 having a web service 226 capability. Remote device 110 includes in certain embodiments a storage device 212 and a mobile patient monitor 214 stored on the storage device 212. The remote device 110 further includes a processor 216, a memory 218, a communication interface (I/F) 220, an output device 222, an input device 224, and a patient identifier 225, which are described in further detail below. Although this particular implementation of remote device 110 is illustrated and primarily described, the present disclosure contemplates any suitable implementation of remote device 110 according to particular needs.

Continuing with reference to FIG. 2, storage device 212 is similar to database 104a and may include any suitable device operable for storing data and instructions. Storage device 212 includes, for example, Random Access Memory (RAM) or Read Only Memory (ROM), EEPROM, a magnetic disk, flash memory, optical disk, or other suitable data storage device.

Mobile patient monitor 214 includes any suitable logic embodied in computer-readable media, that when executed is operable to enable a user to communicate with web service 226 on web server 108 to view and manipulate data, including patient data. For example, mobile patient monitor 214 includes logic for receiving data from input device 224 and translating the data into a message to be sent to web service 226 on web server 108, in turn enabling a user to activate a browser and navigate a web page generated by web service 226 on web server 108 to view patient data. The browser provides, as part of the patient data, a summary of all medical devices 102, imaging device 103, and/or audio device 109 associated with patients under a caregiver's responsibility, or a detailed view that displays specific medical device 102, imaging device 103, and/or audio device 109 configuration data, therapy data, and alarm status data. Mobile patient monitor 214 may be configured to cause remote device 110 to periodically request the most recent webpage data from web service 226 on web server 108. In a particular embodiment, the browser provides an image of the patient, as patient image data, as part of the patient data to the imaging device.

When mobile patient monitor 214 requests patient data (for example, by clicking a navigation link embedded in a web page display), the browser transmits the request to web service 226. In embodiments with a browser, web service 226 may extract the request and transmit a copy of the requested data in a format suitable for display by the browser, as well as any required formatting code, such as HTML code, and/or computational code, such as Javascript, for example. In certain embodiments, formatting code may not be present, such as, for example, in embodiments with a native application at the remote device. Examples of the patient monitor 214 may include a thick client such as a native application that runs of the remote device 110 and which receives data from the web server 108 and conducts its own processing and data manipulation. Alternatively, the patient monitor 214 may be a thin client interface enabling display of data received from the web server 108, and all processing and data manipulation occurs at the application server 106 or the web server 108 and available via a browser such as Mozilla (Firefox), Internet Explorer, Google Chrome, Safari or any other current or future browsers.

Processor 216 includes any suitable device operable to execute instructions and manipulate data to perform operations for mobile patient monitor 214. Processor 216 may include, for example, any type of central processing unit (CPU).

Memory 218 includes any computer memory (for example, Random Access Memory (RAM) or Read Only Memory (ROM)), mass storage media (for example, a hard disk), removable storage media (for example, a Compact Disk (CD), a Digital Video Disk (DVD), or USB Flash Drive), database and/or network storage (for example, a server). Memory 218 may comprise any other computer-readable tangible medium, or a combination of any of the preceding.

I/F 220 includes any suitable device operable to receive input for mobile patient monitor 214, send output from mobile patient monitor 214, perform suitable processing of the input or output or both, communicate to other devices, or any combination of the preceding. I/F 220 may include appropriate hardware (for example, a modem, network interface card, etc.) and software, including protocol conversion and data processing capabilities, to communicate through a LAN, WAN, or other communication system that allows mobile patient monitor 214 to communicate to other devices. I/F 220 may include one or more ports, conversion software, or a combination of any of the preceding.

Output device 222 includes any suitable device operable for displaying information to a user. Output device 222 may include, for example, a touch screen, a video display, a printer, a plotter, or other suitable output device.

Input device 224 includes any suitable device operable to input, select, and/or manipulate various data and information. Input device 224 may include, for example, a touch screen, a keyboard, mouse, graphics tablet, joystick, light pen, microphone, scanner, or other suitable input device.

Patient identifier 225 includes any suitable device for receiving patient identification information. For example, in certain embodiments, patient identifier 225 is an imaging device similar to imaging device 103. In other embodiments, patient identifier 225 may be a barcode scanner, radio frequency identification device receiver, reader, or scanner, or simply a keypad similar to input device 224. In one embodiment, patient identifier 225 is used by a clinician to enter patient identification information of a patient being monitored, such that the identification information may be transmitted to data collection server 104.

Modifications, additions, or omissions may be made to remote device 110 without departing from the scope of the disclosure. The components of remote device 110 may be integrated or separated. Moreover, the operations of remote device 110 may be performed by more, fewer, or other components. For example, although mobile patient monitor 214 is displayed as part of storage device 212, mobile patient monitor 214 may be stored in any suitable location and the operations of mobile patient monitor 214 may be performed by more than one component. Additionally, operations of remote device 110 may be performed using any suitable logic. As used in this document, "each" refers to each member of a set or each member of a subset of a set.

Figure 3:
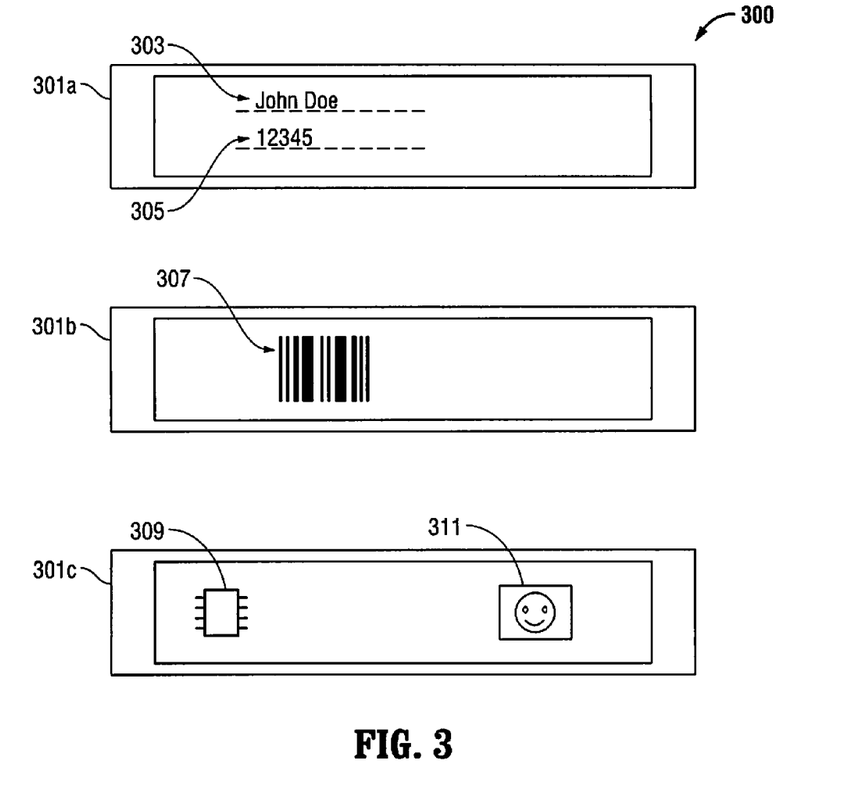
FIG. 3 is an illustration showing various tags associated with a patient, according to certain embodiments of the present disclosure.

Turning now to FIG. 3, various different tags are shown which are illustrated as 301a, 301b, and 301c and which will be described collectively as tags 300. In certain embodiments, tags 300 are wristbands which are affixed, or otherwise secured, to the patient's wrist. Tags include a display of the patient identification information associated with the particular patient. Tag 301a illustrates the patient identification information as being a name 303 and/or a number 305. Tag 301b illustrates the patient identification information as a barcode 307. Although barcode 307 is illustrated as a two dimensional barcode, it is understood that barcode 307 may take the form of a three dimensioned barcode or any other type that is appreciated in the art. Further, tag 301c illustrates the patient identification information as being embedded in a radio frequency identification device chip 309 and/or an image 311, which may be an image of the patient. Although the tags 300 are shown with different forms of patient identification information, it is understood that tags 300 may include some or all of the identification information illustrated, in addition to other means for identification which are known in the art.

Figure 4:
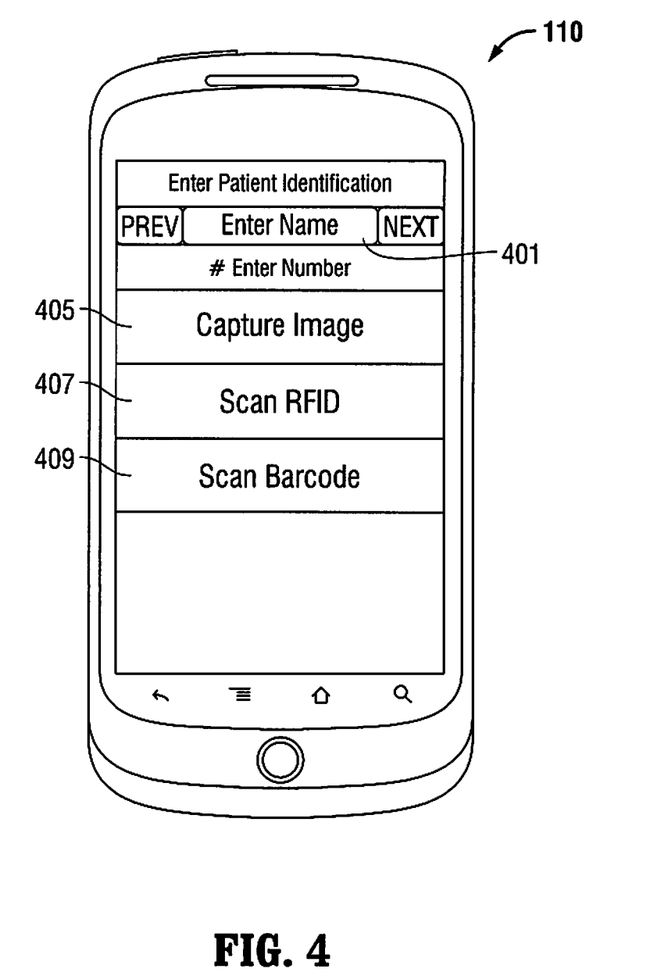
FIG. 4 is an example graphical user interface of a remote device for entering patient identification information, according to certain embodiments of the present disclosure.

Turning now to FIG. 4, a remote device 110 is shown with a GUI configured to receive the patient identification information. Remote device 110, may use any of the patient identifiers 225 (FIG. 2) to read, or otherwise input, the patient identification information displayed on the tags 300. As illustrated, a user may select to enter the name of the patient 401, enter the number of the patient 403, capture an image of the patient 405, scan for an RFID chip 407, and/or scan a barcode of the patient 409. Subsequent to entering the patient identification information via one of the means 401-409 selected, the remote device 110 is also configured to transmit the patient identification information to the data collection server 104.

Figure 5:
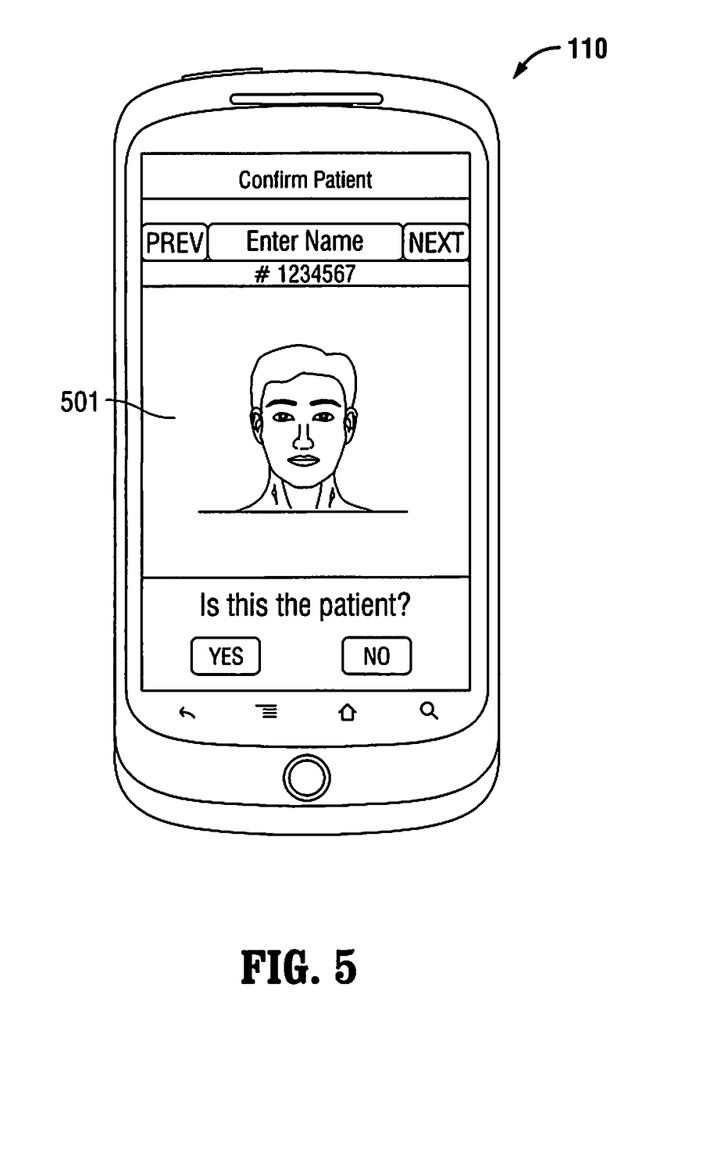
FIG. 5 is a is an example graphical user interface of a remote device after the patient identification information is entered for verifying that the correct patient is associated with the patient identification information, according to another embodiment of the present disclosure.

Turning now to FIG. 5, a remote device 110 is shown with a GUI configured to confirm, or otherwise verify, the image of the patient, i.e. patient image data, which was stored in the database 104a and was previously associated with the patient via the patient identification information. As shown, the GUI in FIG. 4 includes an image 501 of the patient which was received from the data collection server 104. With the image 501 displayed on the display of the remote device 110, the user, i.e. clinician, may select "YES" to confirm that the image 501 matches the patient which is being monitored, i.e. the patient displaying the tag 300 of which the patient identification information was received.

Figure 6:
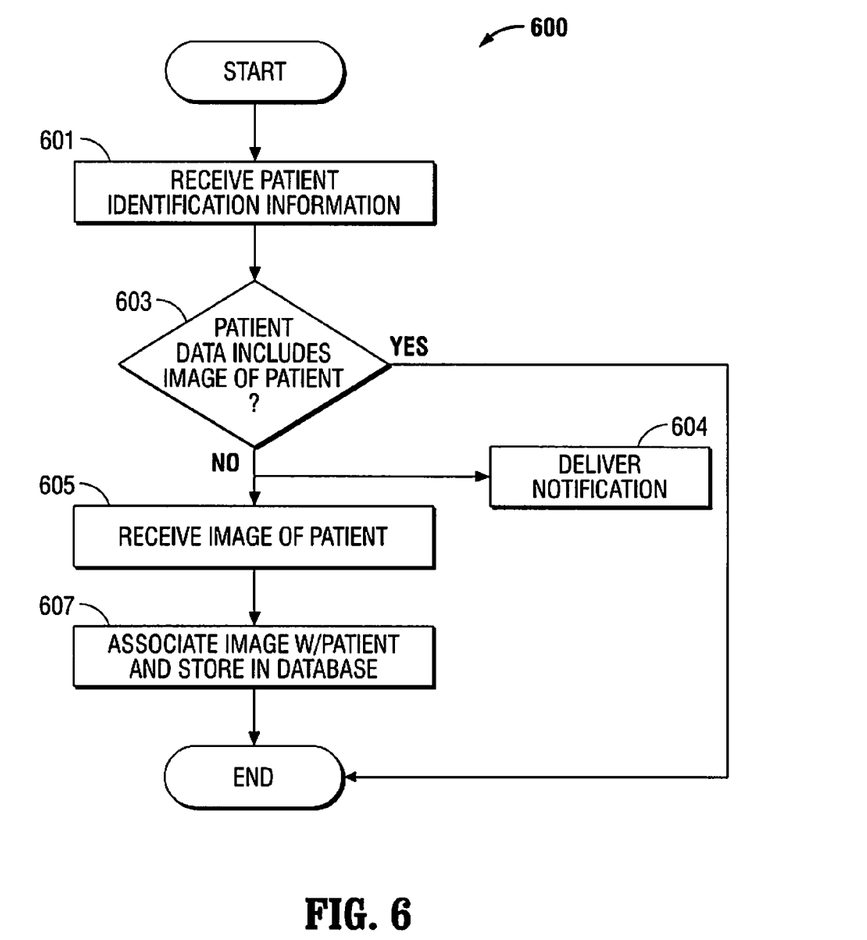
FIG. 6 is a flow chart depicting a method for associating an image of a patient with the corresponding patient identification information, according to certain embodiments of the present disclosure.

Turning now to FIG. 6, a method for associating an image of a patient with the identification information of the patient is shown as method 600. It is envisioned that although method 600, and any of the other methods described herein, are illustrated and described as including particular steps and are described as in a particular order, method 600, and the other methods illustrated and described herein, may include some or all of the steps and may be arranged in any order not specifically described.

Beginning with step 601 of method 600, data collection server 104 receives patient identification information. As described above, the patient identification information may be in the form of the patient name, patient number, barcode, data embedded on an RFID chip, and/or any other suitable form. In one embodiment, a user inputs the patient identification information to a mobile device 110 and transmits the information to the data collection server 104. For Example, a clinician can use the mobile device 110 to scan a barcode displayed on a patient's tag.

In step 603 of method 600, data collection server 104, or another component of system 100, determines whether an image of the patient is associated with the patient identification information received in step 601. In particular, data collection server 104 searches the patient data stored in the database 104a to determine if an image of the patient is stored, i.e. if patient image data is available for this particular patient. If the patient data does include an image of the patient (YES in step 603), then method 600 is complete. Alternatively, if the patient data does not include an image of the patient (NO in step 603), then method 600 proceeds to either or both of steps 604 and 605.

In step 604 of method 600, data collection server 104, or another component of system 100, delivers a notification that no patient image is associated with the patient identification information. In an embodiment, this notification is sent to mobile device 110 for the purpose of informing a clinician that patient image data should be uploaded. For example, a clinician, knowing that no image of the patient is store in database 104a, can now capture an image of the patient and transmit the patient image data to data collection server 104 for storage in the database 104a via remote device 100. In step 605 of method 600, data collection server 104 receives an image of the patient. In an embodiment, this image is captured by imaging device 103. Subsequent to completing step 605, method 600 proceeds to step 607.

In step 607, data collection server 104, or another component of system 100, proceeds to associate the image received in step 605 with the patient identification information received in step 601. In particular, in step 607, data collection server 104, proceeds to associate the patient identification information with the image received and store the pair in the database 104a.

Figure 7:
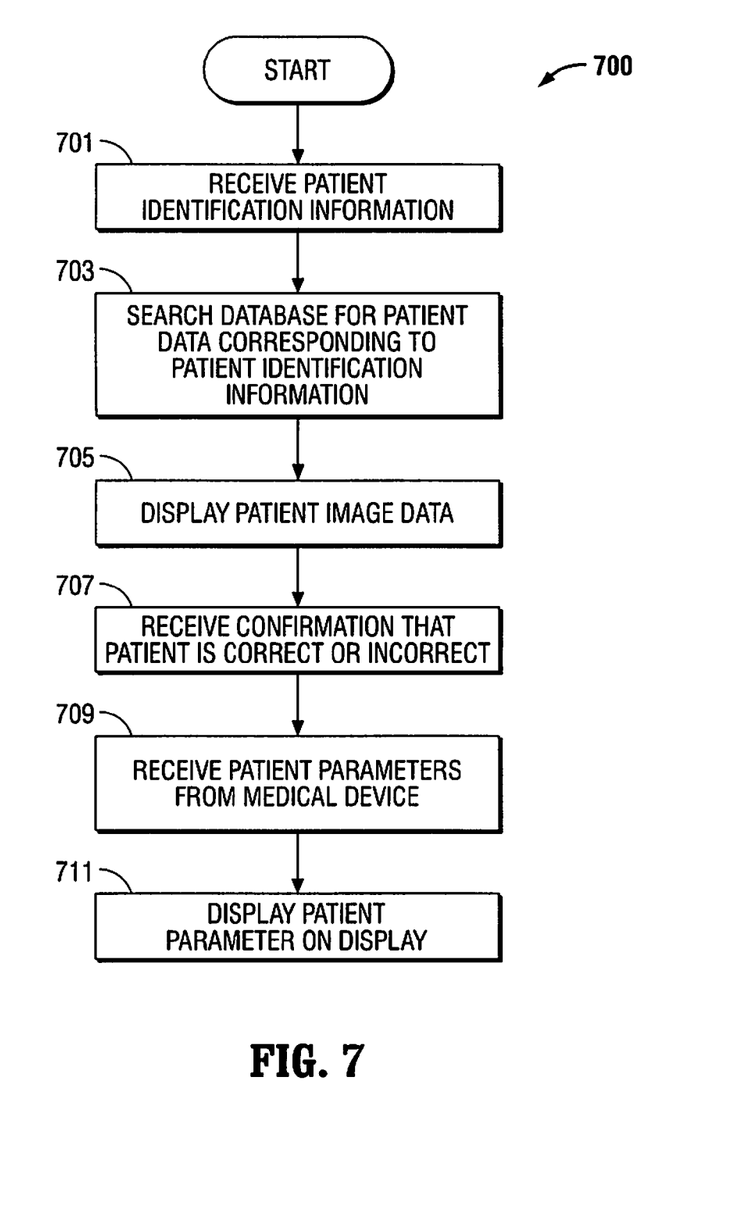
FIG. 7 is a flow chart depicting a method for positive patient identification, according to certain embodiments of the present disclosure.

Turning now to FIG. 7, a method for positive patient identification is illustrated and described as method 700. Method 700 begins with step 701 were data collection server 104 receives patient identification information, similar to step 601 of method 600. In an embodiment, a clinician scans a barcode on a tag of a patient using mobile device 110 and sends the patient identification information to data collection server 104.

In step 703, data collection server 104, searches the database 104a for the patient data corresponding to the patient identification information received in step 701. In an embodiment, data collection server 104 is configured to determine whether a match has been found in the database 104a. For example, after the entire database 104a has been searched, and no match is found, data collection server 104 may be configured to deliver a notification to the clinician, indicating that the patient identification information does not include any corresponding patient data, and may further be configured to prompt the user to associate the patient identification information with patient data stored in the database 104a.

In step 705, data collection server 104 transmits the patient image data from the patient data found in step 703 to mobile device 110. In an embodiment, the mobile device 110 that data collection server 104 transmits the patient data to is the same mobile device 110 that transmitted the patient identification information to the data collection server 104 in step 701. In particular, in step 705 mobile device 110 displays the patient image data transmitted by the data collection server 104 on the display of the remote device 110. As described above, the patient image data displayed includes an image of the patient. In one embodiment, the display of the patient data in step 705 is similar to the GUI illustrated and described in FIG. 3. In certain embodiments, in addition to transmitting patient image data, data collection server 104 transmits other patient data to mobile device 110 as well. For example, data collection server 104 may also transmit the patient's name which is associated with the patient identification information received and the patient's medical history or records.

In step 707, data collection server 104 receives a confirmation notification that the proper image is associated with the patient identification information. In an embodiment, data collection server 104 receives the confirmation notification when a remote device 110 delivers the notification to the data collection server 104. In an embodiment, a clinician receives the patient image data via the remote device 110, and may select to confirm that the patient image data, i.e. the image of the patient, is the same patient that assigned to the patient identification information that the clinician transmitted to data collection server 104. If the notification indicates that the image is correctly associated with the patient identification information, then method 700 proceeds to step 709.

In step 709, data collection server 104 receives the patient parameters from the medical devices 102. In particular, now that it has been confirmed in step 705 that the proper patient is being monitored, i.e. the image of the patient matches the patient identification information, the data collection server 104 will receive updated patient parameters from the medical devices 102 or the database 104a. Subsequent to completing step 709, method 700 proceeds to step 711.

In step 711, data collection server transmits the patient parameters received in step 709 to mobile device 110 for display. In this regard, a safeguard is in place, where the patient parameters that are generated by the medical devices 102 that are monitoring the patient, will only be displayed on the mobile device 110 after a clinician confirms that the patient image data is properly associated with the patient identification information.

In an embodiment, the patient parameters transmitted to the mobile device 100 in step 711 further include an image of the patient which was captured at different time from patient image data already transmitted to the remote device 110 in step 705. For example, the additional image of the patient may be used by a clinician to assist in diagnosing a patient if the clinician detects physical differences in the appearance of the patient between the two images.

Figure 8:
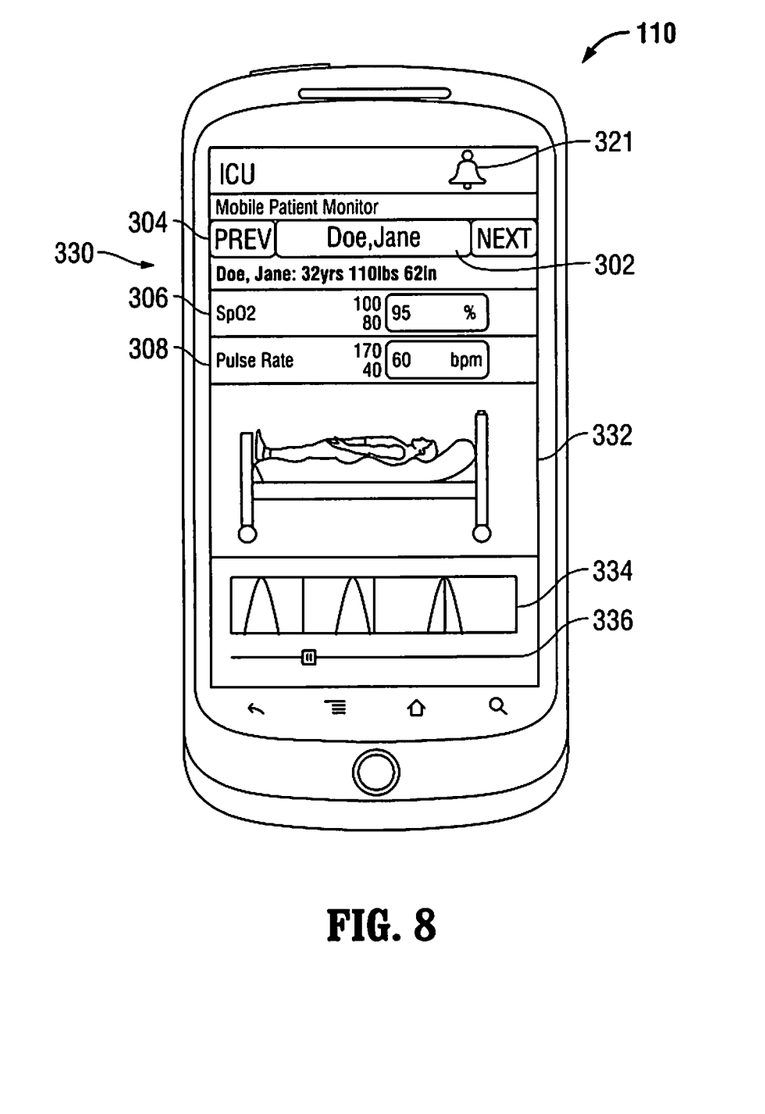
FIG. 8 is an example graphic user interface of a remote device displaying patient data after the patient identification has been verified, according to certain embodiments of the present disclosure.

FIG. 8 illustrates a GUI of the patient parameters displayed on medical device 110 subsequent to completing method 700, in particular at step 711 of method 700.

Certain embodiments of the present disclosure comprise logic for positive patient identification, and may be embodied in at least one tangible, computer-readable medium. For example, when the logic is executed, it may be operable to receive patient identification information, search a database for an image of the patient associated with the patient identification information, receive a confirmation that the patient being monitored is the patient associated with the patient identification information, and transmit patient parameters to be displayed on a mobile device.

In certain embodiments, the logic for positive patient identification may be embodied in more than one tangible, computer-readable medium. For example, portions of the logic for positive patient identification may be embodied in one or more of medical device 102, data collection server 104, application server 106, web server 108, and remote device 110 of system 100 in any manner.

Although the present disclosure describes certain embodiments, various alterations and permutations of the embodiments will be apparent to those skilled in the art. Accordingly, the above description of the embodiments does not constrain this disclosure. Other changes, substitutions, and alterations are possible without departing from the spirit and scope of this disclosure, as defined by the following claims.

What is claimed is:

1. A system for positive patient identification, comprising:
    a database storing a plurality of patient data corresponding to a plurality of patients, wherein each patient data corresponds to a particular patient of the plurality of patients and includes at least one image of the particular patient for confirming an identity of the particular patient;
    a processor; and
    a memory storing instructions executable by the processor, wherein the instructions when executed by the processor cause the system to:
        receive patient identification information;
        search the database for the patient data corresponding to the patient identification information received;
        extract the patient data corresponding to the particular patient identification information received;
        display the patient data on a display including at least one image of the particular patient;
        receive a confirmation indicating whether or not the identity of the particular patient corresponds to the at least one image of the particular patient; and
        display patient physiological parameters being measured by a medical device if the confirmation received indicates that the identity of the particular patient does correspond to the at least one image of the particular patient and restrict a display of patient physiological parameters being measured by a medical device if the confirmation received indicates that the identity of the particular patient does not correspond to the at least one image of the particular patient.

2. The system according to claim 1, wherein the patient data further includes patient history and historical patient physiological parameters.

3. The system according to claim 1, wherein the patient identification information includes a barcode.

4. The system according to claim 1, further comprising at least one medical device configured to generate patient parameters.

5. The system according to claim 1, wherein the instructions when executed by the processor further cause the system to display on the display a first image of the particular patient and a second image of the particular patient, wherein the first image of the particular patient was captured at an earlier time than the second image of the particular patient.

6. The system according to claim 1, wherein the instructions when executed by the processor further cause the system to receive a notification that patient data displayed on the display is properly associated with the patient identification information received.

7. The system according to claim 1, wherein the instructions when executed by the processor further cause the system to receive a new image of the particular patient and store the new image with the patient data in the database.

8. A method for positive patient identification, comprising:
    receiving patient identification information;
    searching a database, including a plurality of patient data corresponding to a plurality of patients, for the patient data corresponding to the particular patient;
    displaying the patient data corresponding to the patient identification information received on a display, wherein the patient data displayed includes at least one image of the particular patient for confirming an identity of the particular patient;
    receiving a confirmation indicating whether or not the identity of the particular patient corresponds to the at least one image of the particular patient; and
    displaying patient physiological parameters being measured by a medical device if the confirmation received indicates that the identity of the particular patient does correspond to the at least one image of the particular patient and restricting a display of patient physiological parameters being measured by a medical device if the confirmation received indicates that the identity of the particular patient does not correspond to the at least one image of the particular patient.

9. The method according to claim 8, wherein the patient data further includes patient history and historical patient physiological parameters.

10. The method according to claim 8, wherein the patient identification information includes a barcode.

11. The method according to claim 8, further comprising receiving patient parameters from at least one medical device monitoring the particular patient.

12. The method according to claim 8, further comprising displaying on the display a first image of the particular patient and a second image of the particular patient, wherein the first image of the particular patient was captured at an earlier time than the second image of the particular patient.

13. The method according to claim 8, further comprising receiving a notification that patient data displayed on the display is properly associated with the patient identification information received.

14. The method according to claim 8, further comprising receiving a new image of the particular patient and storing the new image with the patient data in the database.

15. A non-transitory computer readable storage medium storing a program which, when executed by a computer, causes the computer to perform a method for positive patient identification, comprising:
    receiving patient identification information corresponding to a particular patient;
    searching a database, including a plurality of patient data corresponding to a plurality of patients, for the patient data corresponding to the particular patient;
    displaying the patient data corresponding to the patient identification information received on a display, wherein the patient data displayed includes at least one image of the particular patient for confirming an identity of the particular patient;
    receiving a confirmation indicating whether or not the identity of the particular patient corresponds to the at least one image of the particular patient; and displaying patient physiological parameters being measured by a medical device if the confirmation received indicates that the identity of the particular patient does correspond to the at least one image of the particular patient and restrict a display of patient physiological parameters being measured by a medical device if the confirmation received indicates that the identity of the particular patient does not correspond to the at least one image of the particular patient.

16. The non-transitory computer readable storage medium according to claim 15, wherein the patient data further includes patient history and historical patient physiological parameters.

17. The non-transitory computer readable storage medium according to claim 15, wherein the patient identification information includes a barcode.

18. The non-transitory computer readable storage medium according to claim 15, wherein the instructions when executed by the computer further cause the computer to receive patient parameters from at least one medical device monitoring the particular patient.

19. The non-transitory computer readable storage medium according to claim 15, wherein the instructions when executed by the computer further cause the computer to display on the display a first image of the particular patient and a second image of the particular patient, wherein the first image of the particular patient was captured at an earlier time than the second image of the particular patient.

20. The non-transitory computer readable storage medium according to claim 15, wherein the instructions when executed by the computer further cause the computer to receive a notification that patient data displayed on the display is properly associated with the patient identification information received.

* * * * *